United States Patent
Little et al.

[11] Patent Number: 6,077,669
[45] Date of Patent: *Jun. 20, 2000

[54] KIT AND METHOD FOR FLUORESCENCE BASED DETECTION ASSAY

[75] Inventors: Michael C. Little, Baltimore, Md.; Glenn P. Vonk, Fuquay-Varina, N.C.

[73] Assignee: Becton Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/964,020

[22] Filed: Nov. 4, 1997

[51] Int. Cl.[7] .............................. C12Q 1/68; C12P 19/34; G01N 33/53
[52] U.S. Cl. .............................. 435/6; 435/91.2; 435/968
[58] Field of Search .............................. 435/6, 91, 305.3, 435/968, 975; 536/24.3, 25.32

[56] References Cited

U.S. PATENT DOCUMENTS

| | | | |
|---|---|---|---|
| 5,219,762 | 6/1993 | Katamine et al. | 436/518 |
| 5,229,297 | 7/1993 | Schnipelsky et al. | 436/94 |
| 5,236,827 | 8/1993 | Sussman et al. | 435/34 |
| 5,545,528 | 8/1996 | Mitsuhashi et al. | 435/6 |
| 5,554,502 | 9/1996 | Mitsuhashi et al. | 435/6 |
| 5,593,867 | 1/1997 | Walker et al. | 435/91.2 |
| 5,639,428 | 6/1997 | Cottingham | 422/112 |
| 5,665,562 | 9/1997 | Cook | 435/35 |
| 5,691,145 | 11/1997 | Pitner et al. | 435/6 |
| 5,804,375 | 9/1998 | Gelfand et al. | 435/6 |

FOREIGN PATENT DOCUMENTS

| | | | |
|---|---|---|---|
| 0 298 669 A1 | 7/1988 | European Pat. Off. | B01J 19/00 |
| 0 298 669 B1 | 7/1988 | European Pat. Off. | B01J 19/00 |
| 0 298 669 A1 | 1/1989 | European Pat. Off. | 435/6 |
| 0 347 771 B1 | 6/1989 | European Pat. Off. | G01N 33/52 |
| 0 640 828 A1 | 8/1994 | European Pat. Off. | G01N 21/64 |

OTHER PUBLICATIONS

Amerhsam Life Science Catalog, 1995.
VWR Showcase Catalog, vol. 15, No. 1, 1992.

*Primary Examiner*—W. Gary Jones
*Assistant Examiner*—Jehanne Souaya
*Attorney, Agent, or Firm*—David W. Highet, Esq.

[57] ABSTRACT

The present invention relates to kits and methods for conducting fluorescence based detection assays. The kits are configured in a manner to perform the method so as to reduce or eliminate interfering fluorescence signal.

12 Claims, 4 Drawing Sheets

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (xi) SEQUENCE DESCRIPTION: SEQ ID NO:1:

TACATCAGGC CATATCACC                                        19

(2) INFORMATION FOR SEQ ID NO:2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:2:

```
GCAGCTTCCT CATTGAT                                                          17

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:3:

ACCGCATCGA ATGCATGTCT CGGGTGGTAA AAGTAGTAGA AG                              42

(2) INFORMATION FOR SEQ ID NO:4:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:4:

CGATTCCGCT CCAGACTTCT CGGGGTGTTT AGCATGGTGT T                               41

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:5:

GTCACTCGAG ATTCAGCATT ATCAGAAGGA GCCACCCCAC                                 40

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:6:

ACCGCATCGA ATCGATGTCT CGGGTAGAAA ATCGCATGCA AGATA                           45

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:7:

CGATTCCGCT CCAGACTTCT CGGGAGCTGC CTCAGAATAT ACTCAG                          46

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:
```

```
TAAACATGAA AACTCGTTCC G                                                       21

(2) INFORMATION FOR SEQ ID NO:9:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (xi) SEQUENCE DESCRIPTION: SEQ ID NO:9:

TTTTATGATG AGAACACTTA AACTCA                                                  26

(2) INFORMATION FOR SEQ ID NO:10:

(i) SEQUENCE CHARACTERISTICS:
           (A) LENGTH: 48 base pairs
           (B) TYPE: nucleic acid
           (C) STRANDEDNESS: single
           (D) TOPOLOGY: linear (xi) SEQUENCE DESCRIPTION: SEQ ID NO:10:

TAGCACCCGA GTGCTAGAGT CTTCAAATAT CAGAGCTTTA CCTAACAA                          48

(2) INFORMATION FOR SEQ ID NO:11:

(i) SEQUENCE CHARACTERISTICS:
           (A) LENGTH: 40 base pairs
           (B) TYPE: nucleic acid
           (C) STRANDEDNESS: single
           (D) TOPOLOGY: linear (xi) SEQUENCE DESCRIPTION: SEQ ID NO:11:

CGATTCCGCT CCAGACTTCT CGGGAACAGC TTGAAGTTTT                                   40

(2) INFORMATION FOR SEQ ID NO:12:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (xi) SEQUENCE DESCRIPTION: SEQ ID NO:12:

ACCGCATCGA ATGCATGTCT CGGGTCCTTG CAGTTAGGC                                    39

(2) INFORMATION FOR SEQ ID NO:13:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (xi) SEQUENCE DESCRIPTION: SEQ ID NO:13:

CGCAAATCAT CAAAG                                                              15

(2) INFORMATION FOR SEQ ID NO:14:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (xi) SEQUENCE DESCRIPTION: SEQ ID NO:14:

TCAAGACGCT TCACG                                                              15
```

(2) INFORMATION FOR SEQ ID NO:15:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:15:

TAGCACCCGA GTGCTTTCTC CGTCTGCTCT TTTATCTTCT C          41

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:16:

CGATTCCGCT CCAGACTTCT CGGGACAAAA TCAACACCTG          40

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:17:

ACCGCATCGA ATGCATGTCT CGGGGAGACT GTTAAAGATA          40

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:18:

CAGCAAATAA TCCTTGG          17

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

CATTGGTTGA TGAATTATT          19

(2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:20:

TAGCACCCGA GTGCTCGCAG CCAAAATGAC AGCTTCTGAT GGAA          44

KIT AND METHOD FOR FLUORESCENCE BASED DETECTION ASSAY

FIELD OF THE INVENTION

The present invention relates generally to a kit and method for carrying out a real time fluorescence based assay with liquid biological samples. The kit and method are particularly suited for nucleic acid based (i.e. molecular) diagnostic assays.

BACKGROUND OF THE INVENTION

Processes for nucleic acid based assays are well known and have been implemented in a variety of formats. One of the more common processes conducted in such a nucleic acid based assay is a nucleic acid amplification process. Generally, a nucleic acid amplification reaction is first carried out to completion, and then a nucleic acid probe is used to determine the presence or absence of an amplified nucleic acid sequence of interest. This type of assay is referred to as an end point assay.

One problem with end point assays is that the amplified nucleic acid (amplicons) from the amplification reaction must be physically transferred to the subsequent probe assay. Because of the transfer, the potential exists for contaminating the laboratory environment with the amplicons. In addition, the general risk of misidentifying a given sample or confusing it with other samples increases each time that a physical transfer of the sample takes place.

Thus, there have been previous proposals for self-contained test units that are capable of carrying out an integrated nucleic acid amplification and nucleic acid probe assay on a liquid biological sample while the sample remains confined within the test unit. For example, U.S. Pat. No. 5,229,297, to Paul N. Schnipelsky et al., describes a cuvette for DNA amplification and detection which comprises a plurality of flexible compartments for containing a sample, amplifying reagents and detection reagents, together with passageways connecting the sample and reagent compartments with a detection site and waste compartment. A roller is used to squeeze or compress the sample and reagent compartments in a desired sequence, thereby forcing the sample and detection reagents through the passageways to the detection site and waste compartment. Temporary seals are used to isolate the sample and reagent compartments from the passageways until sufficient pressure is generated by the roller. Although this arrangement is advantageous in that the sample remains within the cuvette during amplification and detection, the need for a roller to break the temporary seals and cause the various fluids to flow between compartments introduces undesirable complexity and makes it difficult to automate the amplification and assay procedure.

Furthermore, in U.S. Pat. No. 5,639,428, an improved test unit for carrying out integrated nucleic acid amplifications and nucleic acid probe based detection assays is disclosed. In the improved test unit, the flow of sample and reagent liquids is controlled by centrifugal force applied by a rotating apparatus, thereby avoiding the need for rollers and other complex mechanisms. While this represents a substantial improvement over the arrangement disclosed in U.S. Pat. No. 5,229,297, the need to provide for controlled fluid movement within the test unit still exists and renders the test unit somewhat more complex than might be desired.

In addition to the end point assays discussed previously, homogeneous real time methods of nucleic acid detection assay also exist. Homogeneous real time methods do not require the physical transfer of the amplified material to a separate assay site, but rather function simultaneously with the amplification reaction, thus, detection can occur in real time. Examples of known homogeneous real time methods include fluorescence polarization, fluorescence energy transfer and light absorbance.

As with the end point assays, there have also been previous proposals for self-contained test units for homogeneous assay methods. For example, U.S. Pat. No. 5,236,827 and its counterpart European Patent No. 0 347 771, describe a device with a fluorogenic substrate for conducting an assay in which an enzyme rate-of-reaction profile is determined to identify microorganisms.

European Patent Application No. 0 640 828 describes an instrument for monitoring multiple nucleic acid amplifications simultaneously. The instrument includes a thermal cycler and a sensor for detecting emitted light from multiple amplifications simultaneously.

U.S. Pat. No. 5,219,762 describes a device and method for measuring the product of an enzymatic reaction wherein the enzyme acts on a target analyte to produce a detectable and measurable enzymatic byproduct.

European Patent No. 0 298 669 describes methods for performing nucleic acid reactions and manipulations in reaction vessels with reagents in a dried state.

Also, in copending U.S. patent application Ser. No. 08/878,096, filed Jun. 18, 1997, a device and method for a homogeneous fluorescence polarization assay is described. This device contains all of the reagents necessary for both a nucleic acid amplification reaction and a nucleic acid probe based assay in dried form, such that all such reagents will be rehydrated by a liquid biological sample at essentially the same time. The device is configured as a flat card in order to minimize the amount of sample in each sample cell of the device, and thereby allow for preheating of the device and rapid equilibration of the temperature of added liquid sample to the temperature of the preheated device (i.e. a "hot start" of the method). However, the rehydration of all dried nucleic acid amplification reagents and all dried nucleic acid probe assay reagents at essentially the same time has been found to cause an unreproducible fluorescence detection signal. This unreproducible signal is believed to be due to variable rehydration of the fluorescently labeled dried nucleic acid probe, and causes interference with the desired fluorescence signal, which interference cannot be factored out, because of the unreproducible nature of the interfering signal. Also, the small volumes used in this device make detection of amplicons from some samples more difficult, and render the device not easily usable by those in the clinical diagnostics field.

In view of the foregoing, a need exists in the art for a kit and method for carrying out an homogeneous nucleic acid amplification and real time nucleic acid probe detection assay with minimal complexity, and which is capable of yielding a consistent, reliable fluorescence detection signal.

SUMMARY OF THE INVENTION

In order to address the disadvantages and limitations of the devices and methods described above, the present invention provides for a kit which is useful for conducting an assay wherein a fluorescence detection method is utilized to determine the presence, absence or quantity of a target analyte in a sample including (1) a first vessel or a first plurality of vessels containing nucleic acid primers and a target analyte binding partner which is capable of producing a detectable change of fluorescence signal, and (2) a second vessel on a second plurality of vessels corresponding to said first vessel or said first plurality of vessels, containing a reagent, or being susceptible to a condition, which initiates a reaction wherein if said target analyte is present in the sample, then the amount of said target analyte will change.

In an alternative embodiment, the kit of the present invention includes a vessel having a first section and at least one other section. The first section contains nucleic acid primers and a binding partner of the target analyte, which binding partner is capable of producing a detectable change of fluorescence signal as the amount of target analyte changes. The other section of the vessel contains a reagent, or is susceptible to a condition, which initiates a reaction wherein if the target analyte is present in the sample, then the amount of target analyte will change.

The present invention also provides a method for detecting the presence, absence or quantity of a target analyte in a sample including steps in which the sample is exposed to a first reagent formulation containing a target analyte binding partner which is capable of producing a detectable change of fluorescence signal as the amount of target analyte changes. Such exposure creates a first mixture which is then exposed to a second reagent formulation or a condition, which, if target analyte is present in the sample, then the amount of target analyte will change.

BRIEF DESCRIPTION OF THE DRAWINGS

The various objects, advantages and novel features of the present invention will be readily understood from the following detailed description when read in conjunction with the appended drawings in which.

DETAILED DESCRIPTION OF THE INVENTION

Figure 1:
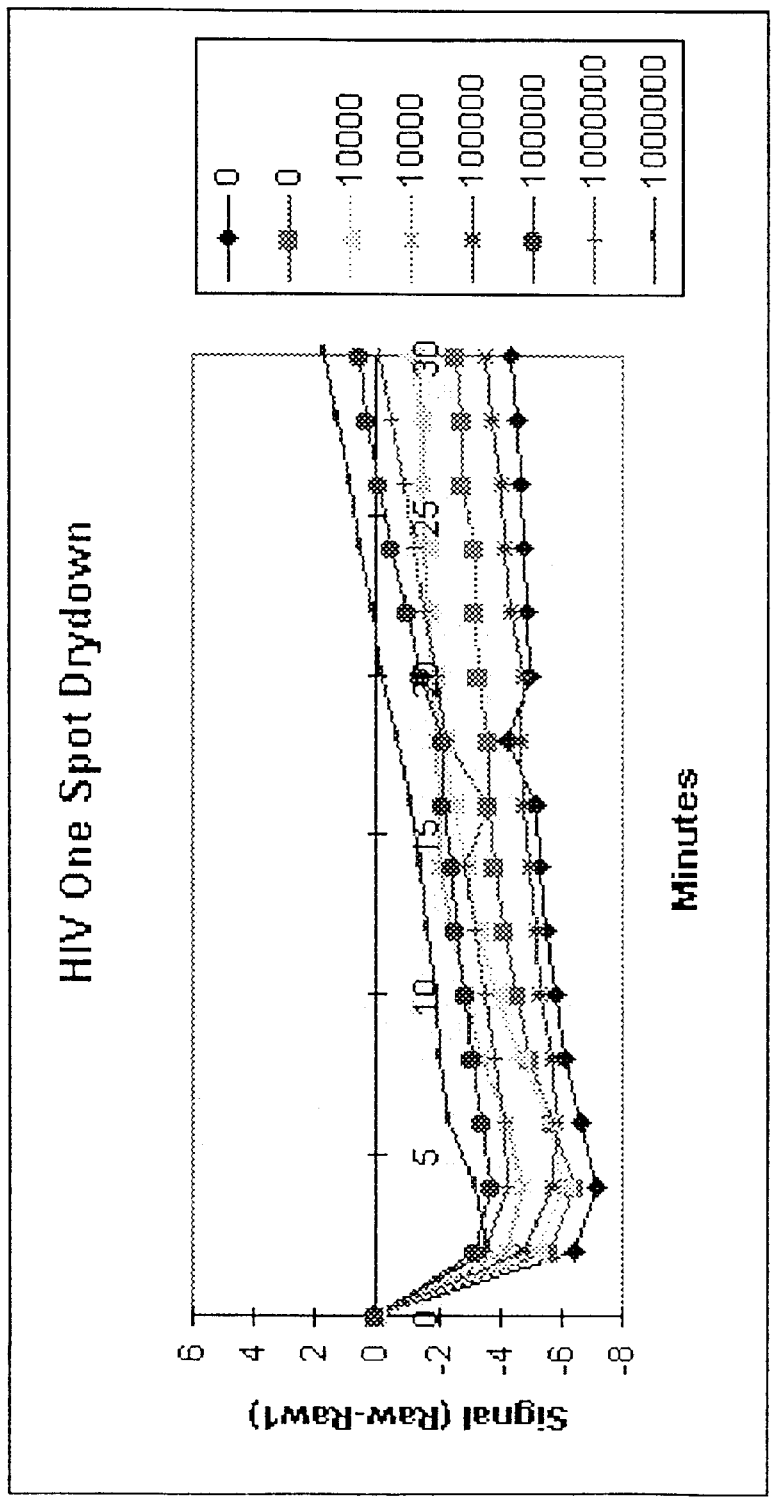
FIG. 1 depicts the results of a comparative experiment in which an amplification and homogeneous fluorescence real time detection assay was conducted in a known device wherein all assay reagents were dried in a single spot in the device.

The present invention relates to assays in which detection of a fluorescence signal is conducted in real time (i.e., as a reaction is occurring). In such assays, a change in fluorescence signal is detected.

In order for such real time fluorescence detection assays to be useful, the change in fluorescence signal over time must be detectable and capable of being monitored. Thus, interfering fluorescence background (i.e., fluorescence signal due to conditions other than the presence of a target analyte) is detrimental to real time fluorescence detection assays if it is not constant or reproducible. That is, interfering background may be of significant magnitude relative to the specific signal as long as the change in fluorescence background is (1) small relative to the change in specific signal, or (2) may be compensated for through use of a numerical algorithym.

However, when real time fluorescence detection assays are formatted with reagents in a dry form to be rehydrated, the rehydration of the dry fluorescently labeled reagent causes an interfering fluorescence background which is not constant and changes irreproducibly. Thus, this interfering background masks the specific fluorescence change and cannot be corrected for by numerical methods. Therefore, the method and kit of the present invention are designed to eliminate this cause of interfering fluorescence background by postponing initiation of the detection reaction which produces the desired change in fluorescence signal until after rehydration of the fluorescently labeled reagent.

In the method of the present invention, a sample which may contain a target analyte is exposed to a first reagent formulation which includes nucleic acid primers and a fluorescently labeled binding partner of the target analyte. Such exposure creates a first mixture. Then, the first mixture is exposed to a second reagent formulation or to a condition, which, if the target analyte is present, will cause a detectable change in fluorescence signal to be produced.

In such a method, the fluorescently labeled reagent (i.e., the fluorescently labeled binding partner for the target analyte) is rehydrated prior to initiation of the detection reaction. That is, the detection reaction is postponed until after rehydration of the fluorescently labeled binding partner.

The fluorescently labeled target analyte binding partner of the first reagent formulation is any entity which has a binding specificity for the target analyte sufficient to discriminate the target analyte from other related analytes. When the target analyte is a nucleic acid molecule, a typical binding partner is a nucleic acid molecule having sufficient complementarity that the binding partner nucleic acid molecule will hybridize to the target analyte nucleic acid molecule.

Methods for fluorescently labeling nucleic acid molecules (i.e. conjugation) are well known to those skilled in the art. Examples of suitable fluorescence labels for use in the present invention include xanthene dyes such as fluoresceins, rhodamines and rosamines, and napthylamines such as 1-dimethylaminonapthyl-5-sulfonate, 1-anilino-8-napthalene sulfonate and 2-p-toluidinyl-6-napthalene sulfonate.

The fluorescently labeled nucleic acid molecule binding partner is present in the first reagent formulation with nucleic acid primers specific for a target nucleic acid of interest. However, there may be other reagents in the first reagent formulation, so long as a certain second reagent formulation which would initiate the detection reaction, or a condition which would initiate the detection reaction, is withheld from the first reagent formulation and the mixture created by exposure of the sample to the first reagent formulation. For example, if a polymerase based nucleic acid amplification reaction is part of the detection assay, the second reagent formulation may include a polymerase, because exposure of the sample to a first reagent mixture which does not contain a polymerase will not cause initiation of the detection assay, but will permit rehydration of a dried fluorescently labeled nucleic acid molecule binding partner. Similarly, if such a detection assay is not initiated until a certain temperature is applied, then rehydration of the first reagent formulation including the fluorescently labeled nucleic acid molecule binding partner by exposure to the sample may be carried out a lower temperature, and then the mixture is exposed to heat as the condition to initiate the detection assay.

Initiation of the detection assay is the commencement of a change in the amount of target analyte. When the target analyte is a nucleic acid molecule, the change in amount of target analyte is an increase of amount caused by the production of amplicons (i.e., copies of the target nucleic acid molecule analyte) by a nucleic acid amplification reaction. Such nucleic acid amplification reactions are well known to those skilled in the art, and suitable examples of such reactions include Strand Displacement Amplification ("SDA"), Polymerase Chain Reaction ("PCR"), Ligase Chain Reaction ("LCR"), Transcription Mediated Amplification ("TMA") and Nucleic Acid Sequence Based Amplification ("NASBA"). In such reactions, the production of amplicons (i.e., an increase in the amount of target analyte) causes a change in fluorescence signal which may be detected as the amount of target analyte increases with time (i.e., real time detection).

For example, in an assay based on fluorescence energy transfer ("FET"), a change in the intensity of a fluorescence signal is detected. In such assays a fluorescence energy donor moiety and a fluorescence energy acceptor moiety are present on the target analyte binding partner. When the donor and acceptor moieties are in sufficiently close proximity, the intensity of the fluorescence signal from the donor moiety is quenched by the acceptor moiety. Thus, FET assays are designed such that: (1) an increase in the intensity of the fluorescence signal indicates the presence of a target analyte (i.e., the donor and acceptor moieties are initially in close proximity, and the presence of the target analyte causes a decrease in such proximity); or (2) a decrease in the intensity of the fluorescence signal indicates the presence of a target analyte (i.e., the donor and acceptor moieties are initially not in close proximity, and the presence of the target analyte causes an increase in such proximity).

In order to be capable of an increase or decrease of the proximity of the fluorescence energy donor and acceptor moieties, the binding partner is capable of some change of secondary structure. Examples of nucleic acid molecule secondary structure which retain a fluorescence donor moiety and a fluorescence acceptor moiety in sufficient proximity to quench fluorescence signal are G-quartets and stem-loop or hairpin structures. Nucleic acid molecules of such secondary structures are well known to those skilled in the art from references such as Varani, G., *Annu. Rev. Biophys. Biomol. Struct.* 1995, 24:379–404, and Williamson, J., *Annu. Rev. Biojphys. Biomol. Struct.* 1994, 23:703–30. These secondary structures are also capable of deformation to render a linear secondary structure in which the proximity of the fluorescence energy donor moiety and fluorescence energy acceptor moiety is decreased resulting in less quenching of the fluorescence signal. A 5–10 fold enhancement of the fluorescence signal may be observed upon deformation of hairpin structure in the presence of amplicons using fluorescence donor-acceptor pairs such as fluorescein—Rox or DABCYL—fluorescein as taught in U.S. Pat. No. 5,928,869 and U.S. Pat. No. 5,846,726, the disclosures of which are specifically incorporated herein by reference.

Particularly when the mixture of sample and first reagent formulation is exposed to a second reagent formulation rather than to a condition, physical separation of the first reagent formulation from the second reagent formulation may be accomplished by a variety of means. In one embodiment, corresponding first and second vessels such as wells may contain, respectively, the first reagent formulation and the second reagent formulation. In such a configuration, the corresponding first and second wells may be marked with corresponding indicia of their relatedness. For example, the corresponding first and second wells may be marked with bar codes or other codes, or color-coded to indicate their relatedness. Such indicia of relatedness is useful to reduce the possibility of incorrect transfer of reaction mixture from a first well to a second well when corresponding multiple well plates or other devices are being used.

Alternatively, a single vessel such as a well may be divided into two or more sections. In such an embodiment, the first reagent formulation is in a first section of the well, and the second reagent formulation is in a second section of the well. Although the sections of the well may be marked as described above, it may not be as important in this embodiment, because the mixture created from the exposure of the first reagent formulation to the sample will only be transferred to another section of the same well rather than to a second well. Thus, there is a lesser risk of error in the transfer, and a lesser need for marking corresponding sections to reduce such risk.

In either of the above embodiments, the first reagent formulation and the second reagent formulation are typically in a dry format in the form of a spot on an interior wall of a vessel. The reagents in the dried first reagent formulation spot and the dried second reagent formulation spot are carried in a readily soluble matrix, such as trehalose or another carbohydrate. These reagents will readily rehydrate when exposed to an aqueous liquid in a well. However, either embodiment is also useful when the second reagent formulation is not in a dry form.

When performed in a preferred embodiment, the method of the present invention involves a nucleic acid amplification reaction wherein an nucleic acid molecule binding partner having a fluorescence donor moiety and a fluorescence acceptor moiety is utilized. A first well contains such a binding partner in a dried form and all other reagents except for nucleic acid amplification enzymes in a dried form (i.e., the first reagent formulation). Such enzymes (i.e., the second reagent formulation) are in a dry form in a corresponding second well. A liquid sample which may contain a target analyte (i.e., nucleic acid molecule) is added to the first well causing the first reagent formulation to rehydrate and forming a mixture of sample and first reagent formulation. The mixture is then transferred to the second well and causes the rehydration of the second reagent formulation, thus initiating a homogeneous nucleic acid amplification and real time fluorescence detection assay. The second well is read by a fluorescence detection instrument. If the target analyte is present, amplicons are produced, and increasing fluorescence signal will be detected as the fluorescence donor moieties and the fluorescence acceptor moieties become more distant from each other, thus decreasing the quenching of fluorescence signal. The initial quantity of target analyte may therefore be estimated using numerical analysis of increased fluorescence signal over time. Numerical methods for estimation of initial target number from fluorescence rate data include overall slope, calculation of the time to first positive, and maximum rate of change.

For example, in one type of quantitation analysis, a plurality of known quantities of a nucleic acid sequence in respective calibration samples (i.e., standards) and an unknown quantity of the nucleic acid sequence in a test sample are amplified in parallel during a time interval.

Indicia of the quantities of the nucleic acid sequence being amplified in the calibration and test samples are then measured using conventional techniques, at measurement points in the time interval. The indicia of the quantities of the nucleic acid sequence being amplified may take the form of fluorescence signals (e.g., fluorescence intensities or detectable fluorescent energy transfer) if the samples contain fluorescent indicators therein (e.g., fluorescent dyes, labels, intercalators, etc). Other indicia that are suitable for real-time measurement (e.g., radioactive signals) may also be used.

A step is then performed to determine for a first potential cutoff level, a corresponding first set of time points in the time interval at which the measured indicia of the quantities of the nucleic acid sequence being amplified in each of the calibration samples equal the first cutoff level. This step is then repeated for each of a number of different potential cutoff levels so that respective sets of time points in the time interval can be obtained for each potential cutoff level. According to a preferred aspect of this quantitation analysis, a step is then performed to determine, relative to a statistical criterion, which of the sets of points in the time interval better satisfies the statistical criterion against the known quantities of the nucleic acid sequence in the calibration samples. A quantity of the nucleic acid sequence in the test sample is then determined based on the set of points determined to better or best satisfy the statistical criterion.

For example, the step to determine which of the sets of points better satisfies the statistical criterion may comprise the step of determining which of the sets of points in the time interval provides a better linear fit against logarithms of the known starting quantities of the nucleic acid sequence in the calibration samples. Preferably, this step comprises the steps of fitting regression lines to respective "graphs" of each of the sets of time points in the time interval versus logarithms of the known starting quantities of the nucleic acid sequence in the calibration samples. Standard deviations of the fits between each of the sets of time points and respective regression lines are then determined. The set of time points preferably corresponding to the lowest standard deviation of fit is then used to select the preferred cutoff level from the potential cutoff levels and then determine the starting quantity of the nucleic acid in the test sample based on the preferred cutoff level. This advantageous result is preferably achieved by determining a time at which the measured indicia of the quantities of the nucleic acid sequence in the test sample equals the preferred cutoff level and then fitting that time to the "preferred" regression line corresponding to the preferred set of time points. The logarithm of the starting concentration of the nucleic acid sequence in the test sample can then be determined from the preferred regression line.

According to another quantitation analysis, a curve fitting operation is performed to more accurately estimate the preferred indicia cutoff level (e.g., preferred fluorescence signal cutoff level). In particular, respective "data" curves are preferably fit to "graphs" of discrete points of the measured fluorescence signals of individual calibration and test samples versus points in the time interval at which the corresponding fluorescence signals were measured. Here, a non-parametric curve smoothing operation may be performed after the discrete points have been normalized to a common baseline. It is also possible to even further improve the accuracy of the preferred indicia cutoff level by determining lower confidence limit curves for each of the "smoothed" data curves. The lower confidence limit curves may also be smoothed using a non-parametric smoothing operation. Each of the above-described sets of time points in the time interval can then be determined by determining intersections between each of the smoothed lower confidence limit curves and the respective potential cutoff levels.

As described above, a set of time points corresponding to a lowest standard deviation of fit can be used to accurately determine a preferred cutoff level and then determine the starting quantity of the nucleic acid in the test sample based on the preferred cutoff level. However, according to another type of quantitation analysis, control samples containing known starting quantities of the nucleic acid sequence can also be used to facilitate determination of a preferred cutoff level. In particular, after respective regression lines have been fit for each set of time points in the time interval corresponding to the calibration samples, an average prediction error (APE) can be determined between each regression line and those of a respective set of time points corresponding to the control samples. The potential cutoff level corresponding to the regression line having the lowest average prediction error associated therewith can then be used to determine the starting concentration of the nucleic acid sequence in the test sample.

As is apparent from the description of the method above, the reagent formulations and vessels are suited for combination in a kit, particularly when such vessels are the wells of standard 96 well microwell plates. Such a kit includes the corresponding first and second vessels with the first reagent formulation dried in the first vessel, and the second reagent formulation either dried in the second vessel or included in the kit but as a liquid formulation in an additional container in the kit.

The dried first reagent formulation is adhered to an interior wall of each first vessel in the form of a single, discrete spot. The dried second reagent formulation is adhered to an interior wall of each corresponding second vessel in the form of a single, discrete spot. Liquid samples can be introduced into each of the first vessels (preferably by pipetting). Similarly, after rehydration of the first reagent formulation by exposure to the sample, the mixture of these two entities can be introduced into each of the corresponding second vessels. As will be described hereinafter, the liquid biological sample that is introduced into the first sample vessel makes contact with, and dissolves, the dried first reagent formulation spot in the sample vessel.

A sealing means such as a strip is also provided for sealing the second vessels after the mixture of first reagent formulation and sample has been introduced into the second vessels. Preferably, the sealing means is a material provided with a layer of pressure sensitive adhesive on its lower surface. In one embodiment, a flexible sealing strip is applied in a manner similar to adhesive tape, and serves to permanently seal the second vessels.

The sealing of the second vessels by means of the sealing strip provides several advantages. The primary advantage of the sealing strip is that it prevents the release of nucleic acid amplicons from the second vessels, thereby preventing contamination of the laboratory environment. Secondarily, the sealing strip prevents evaporation of the liquid mixture from the second vessels during the homogeneous nucleic acid amplification and real time fluorescence detection assay. However, given that the volume of mixture in a typical well of a microwell plate is fairly large in comparison to other known devices such as cards (e.g. approximately 300 $\mu$l volume of a well in contrast to approximately 20 $\mu$l volume of card sample cell), evaporative loss from microwells is not as significant an issue as it is for a card device.

Typically, the various liquid biological samples used in the kit and method of the present invention will consist of urine samples, blood samples or other body fluid samples from different patients, all of which are being tested for the same pathogen by a homogeneous nucleic acid amplification and real time fluorescence detection assay. However, it is understood that embodiments are possible in which more than one of the liquid biological samples are drawn from the same patient, and in which the first reagent formulation differs from one first vessel to the next.

For detection of any change in fluorescence signal in the second vessel, any suitable, commercially available fluorescence measuring instrument may be used, such as a microplate fluorometer or a microplate reader. Alternatively, a specialized instrument may be designed. Depending on the temperature requirements of the homogeneous nucleic acid amplification and real time fluorescence detection assay, heating means, usually in the form of heat blocks, are provided for the first sample vessels and/or second vessels, as well as within the instrument.

In an assay based on fluorescence polarization ("FP"), a change in the FP value is detected. In fluorescence polarization assays, a polarized excitation beam of a given wavelength of light is used to excite the fluorescently labeled oligonucleotide binding partner. The intensity, at a given wavelength, of fluorescent emission from these excited binding partners is measured in the plane polarized parallel to the excitation polarization, and also in the plane polarized perpendicular to the excitation polarization. When a fluorescently labeled oligonucleotide binding partner hybridizes to a nucleic acid amplicon, the intensity of fluorescent emission in the plane parallel to the excitation plane increases. Typically, both parallel and perpendicular intensities are measured. The changes in total intensity are then compensated for by applying the formula:

$$P=(I_{PARA}-I_{PER})/(I_{PARA}+I_{PER}),$$

where:

$I_{PARA}$=Fluorescent intensity in the plane polarized in the plane polarized parallel to the plane of excitation polarization; and $I_{PER}$=Fluorescent intensity in the plane polarized in the plane polarized perpendicular to the excitation polarization.

This formula yields the dimensionless quantity referred to as the polarization ratio (P).

Since it is the polarization intensity in the plane parallel to the excitation polarization which increases with increased hybridization, measuring the intensity of the polarization in the plane parallel to the excitation polarization over time will show the increase in hybridization of oligonucleotide binding partner to oligonucleotide target analyte over time. This is a kinetic or dynamic approach to the measurement of fluorescence polarization, which is also suitable for use with fluorescence energy transfer and light absorbance assays. By using such a kinetic or dynamic approach, compensation for absolute intensity becomes somewhat less important because each sample is measured against itself and is thus a relative measurement. In the case of a fluorescence polarization assay, therefore, it becomes necessary to measure fluorescence intensity only in the plane polarized parallel to the plane of the excitation polarization.

The following Examples illustrate specific embodiments of the invention described herein. As would be apparent to skilled artisans, various changes and modifications are possible, and are contemplated within the scope of the invention described.

EXAMPLE 1

Comparative Example Using a Kit and Method Wherein Rehydration of Dry Fluorescence Detector Probe and Amplification of a Target Analyte Occurs in a First Vessel of Such Kit During a First Step of Such Method This Example was performed as an exemplification of problems associated with existing kits and methods used for conducting fluorescence detection assays. The kit used for this Example included a device for a homogeneous fluorescence polarization assay as described in copending U.S. Pat. No. 5,948,673 ("DNA Card"). The method practiced for this Example is also as taught in the referenced patent application. Briefly, as described in the Background section above, the DNA Card is a device which contains all of the reagents necessary for both a nucleic acid amplification reaction and a nucleic acid probe based assay in dried form, such that all such reagents will be rehydrated by a liquid biological sample at essentially the same time.

Materials and Methods

In this Example HIV was the target analyte using Strand Displacement Amplification ("SDA") in a homogeneous real time fluorescence detection assay. Sequence numbering for the HIV gag gene adheres to that described in Gurgo C., Guo H. G., Franchini G., Aldovini A., Collalti E., Farrell K., Wong-Staal G., Gallo R. C., and Reitz M. S. Jr. (1988) Virology 164, 531–536. A portion of the HIV GAG-1 gene was cloned into a pGEM11Zf(+) vector for use as target. The cloned GAG sequence was identical to HIV MN and corresponds to positions 1222–1839, as described by Gurgo et.al.

Bumper Primer B1, 5'dTACATCAGGCCATATCACC (SEQ ID NO: 1), corresponds to gag positions 1223–1241. Bumper Primer B2, 5'dGCAGCTTCCTCATTGAT (SEQ ID NO: 2), corresponds to positions 1424–1408. Amplification Primers S1, 5'dACCGCATCGAATGCATGTCTCGGGTG-GTAAAAGTAGTAGAAG (SEQ ID NO: 3), and S2, 5'dCGATTCCGCTCCAGACTTCTCGGGGT-GTTTAGCATGGTGTT (SEQ ID NO: 4) correspond to gag positions 1260–1276, and positions 1368–1348, respectively.

Final HIV SDA reaction conditions were as follows: 35 mM KPO4 (pH7.6), 0.1 mg/ml acetylated bovine serum albumin, 1 uM primer S1, 0.75 uM primer S2, 0.05 uM each primer B1 and B2, 400 nM of the FAM-ROX detector probe (5'-FAM-dGTCACTCGAGAT(ROX)TCAGCATTATCAGAAGGAGCCACCCCAC-3' (SEQ ID NO: 5)), 1.4 mM dCTPαS, 0.5 mM dUTP, 0.2 mM each dATP and dGTP, 7.5 mM MgOAc, 5% DMSO, 8% glycerol, 500 ng human placental DNA, 320 units BsoB1, and 20 units BST per 50 uL final reaction volume. In dry-down experiments, sufficient trehalose was added to produce hard glassy films following dehydration. The amount of trehalose used was 1% (w/v) of the final SDA volume.

Devices and Instrumentation

DNA Cards were die cut from cellulose acetate butyrate sheets and assembled using film backed adhesive. Two sheets form a depression in which reagents were dried. Addition of a third sheet completes a DNA Card having 64 sample compartments. Each sample compartment is capable of holding a 20 uL volume, and is accessed through a sample addition port. A second port is provided as a vent. After sample addition, an adhesive backed sealer strip was placed over both openings to prevent evaporation and contamination of future SDA reactions. Fluorescence measurements were performed through the transparent sheets of the DNA Card during amplification.

A Fluoroskan microwell fluorometer (Labsystems, Rochester, N.Y.) was modified to perform real time SDA in DNA Cards. These modifications included adjustment of the stage height, and introduction of a heat stage to control temperature in the DNA Card to ±0.3° C. at any set point between 50 and 60° C. The fiber optics bundle was offset by 15 degrees from vertical to reduce background resulting from reflected light off of the DNA Card. Bandpass interference filters were used to discriminate excitation (485 nm) and emission light (535 nm). Modifications to Genesis™ software (Labsystems, Rochester, N.Y.) facilitated real time measurement of fluorescence intensity in up to 64 sample compartments. The detection limit for fluorescein isothiocyanate was approximately 20 nM at twice the background fluorescence with linearity extending above 1000 nM. Typical cycle times were 1 second per measurement, or about 1 minute to read an entire DNA Card of 64 samples.

Procedure

The SDA reagents described above were assembled into a 5x mix excluding KPi, DMSO and glycerol. The concentration of KPi buffer in the dry-down mix was 37.5 mM. Aliquots of this mix (4 uL) were added to individual DNA Card sample compartments and dried to glassy films in a single spot. HIV target was prepared in 31 mM KPi, 5.8% glycerol and 5% DMSO. Target aliquots were added to each sample compartment, the compartments sealed, and the fluorescence monitored (485 (EX)/535 (EM) ) for 30 minutes.

Results and Conclusions

As shown in FIG. 1, the results indicate a variable and negative signal fluctuation during the first 5 minutes of the amplification reaction. Such a variable signal fluctuation was not amenable to compensation through use of a numerical algorithym. Furthermore, such variable signal fluctuation renders the diagnostic results of such an assay unreliable.

EXAMPLE 2

Further Comparative Example Wherein Background Amplification is Substantially Eliminated This Example was performed as a further exemplification of problems associated with existing kits and methods used for conducting fluorescence detection assays. The kit used for this Example was the same as that used for Example 1. Also, the Methods and Materials and Devices and Instrumentation were the same as those used in Example 1.

Due to the variable signal fluctuation and resultant unreliable diagnostic results in Example 1, an experiment was performed in which background amplification was substantially eliminated by drying the SDA reagents in two spots, rather than one spot, in the sample compartment of the DNA Card.

Specifically, the Procedure of Example 1 was followed except that a first dry spot (3 uL) contained all reagents needed for amplification except dUtp, which was incorporated into a second dry spot (1 uL). Trehalose was maintained at the same final concentration, but divided proportionately according to the volume in each spot. The rehydration buffer was assembled in accordance with Example 1.

Results and Conclusions

Figure 2:
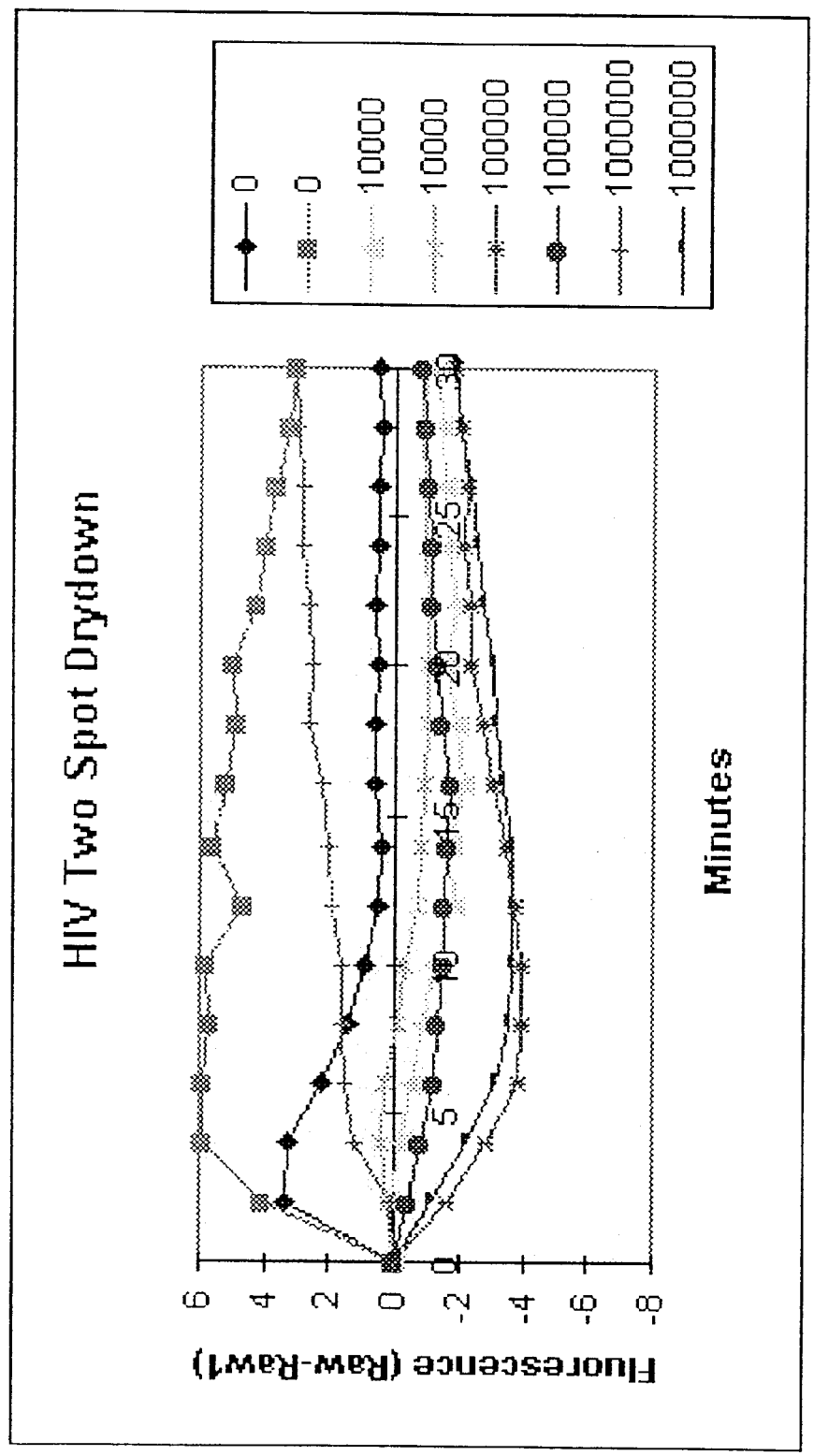
FIG. 2 depicts the results of a second comparative experiment in which an amplification and homogeneous fluorescence real time detection assay was conducted in a known device wherein the assay reagents were dried in two spots in the device.

As shown in FIG. 2, the results indicated both a large positive and negative variation in fluorescence signal during the first 10 minutes of the amplification reaction. As in Example 1, such a variable signal fluctuation was not amenable to compensation through use of a numerical algorithym. Furthermore, such variable signal fluctuation renders the diagnostic results of such an assay unreliable. This result also suggested that it may be the rehydration of the fluorescence probe during the amplification reaction which was creating such variable signal fluctuation.

EXAMPLE 3

Stabilization of Fluorescence Signal in a Method for Amplification and Homogeneous Real Time Fluorescence Detection of a Target Analyte (HIV)

In order to test the hypothesis that rehydration of the fluorescence probe during amplification of a target analyte was causing the variable signal fluctuation seen in Examples 1 and 2, an experiment was conducted as in Example 1 above, but only the SDA enzymes (i.e., BsoB1 and Bst) were dried in the presence of 37.5 mM Mg(OAc)$_2$, 0.25 mg/mL BSA, 7.5 mM KPi, with 5% (w/v) trehalose by aliquoting 4 uL of mix to each sample compartment of the DNA Card. The remainder of the SDA reagents were added to the sample compartment in wet form with the target analyte and sample.

Results and Conclusions

Figure 3:
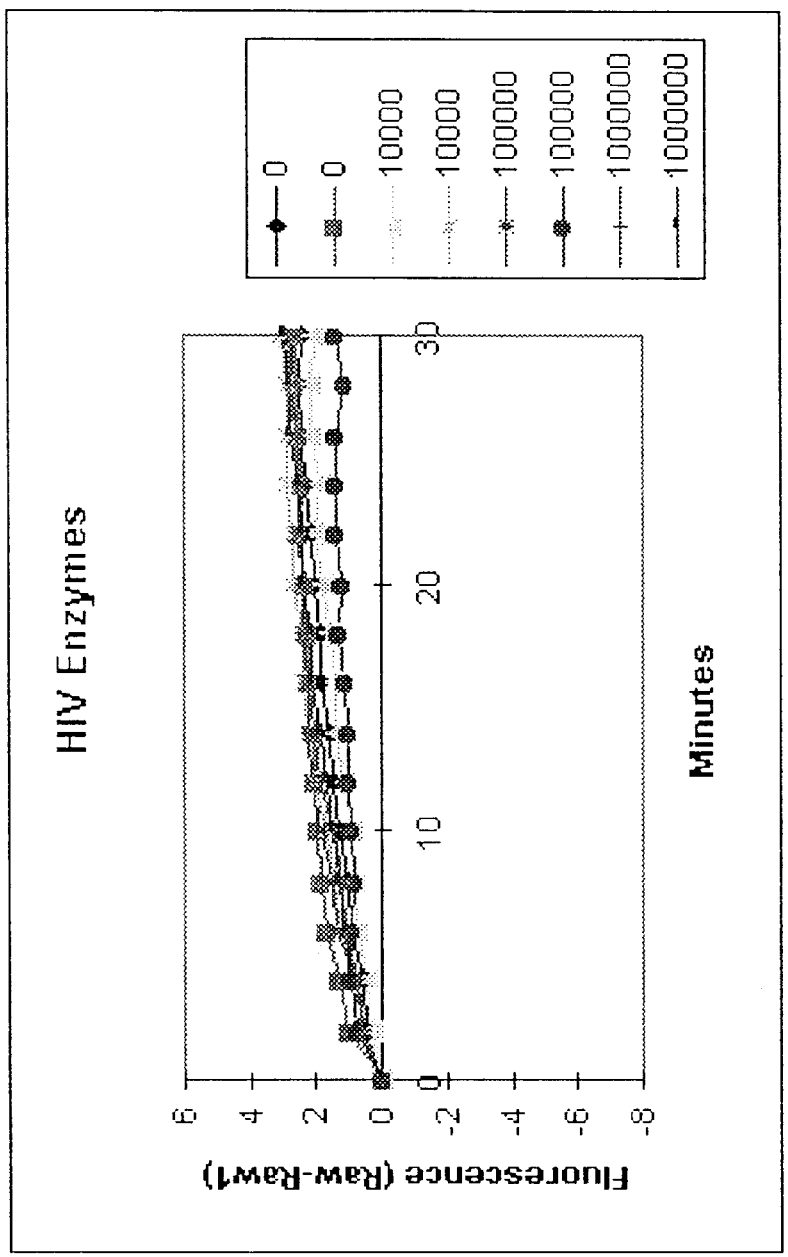
FIG. 3 depicts the results of an experiment in which an amplification and homogeneous fluorescence real time detection assay was conducted wherein a HIV nucleic acid sequence was amplified with a rehydrated fluorescence probe.

As shown in FIG. 3, the results indicated a more stable fluorescence signal during the first 10 minutes of amplification. Thus, more reliable diagnostic assay results may be achievable when rehydration of a fluorescence probe and amplification of a target analyte are not conducted simultaneously.

EXAMPLE 4

Stabilization of Fluorescence Signal in a Method for Amplification and Homogeneous Real Time Fluorescence Detection of a Target Analyte (Chlamydia)

In order to confirm the results of Example 3, a similar experiment was conducted for the amplification and homogeneous real time detection of a Chlamydia nucleic acid sequence.

Materials and Methods

For this Example, Chlamydia elementary bodies (E serovar) were obtained from the University of North Carolina and lysed at 95° C. for 5 minutes prior to use as target stocks. The target sequence is from a conserved region of the chlamydia cryptic plasmid.

In the SDA reaction, amplification primers S1.1 5'-dACCGCATCGAATCGATGTCTCGGGTAGAAAAT-CGCATGCAAGATA (SEQ ID NO: 6) and S2.1 5'-dCGATTCCGCTCCAGACTTCTCGGGAGCTGCCT-CAGAATATACTCAG (SEQ ID NO: 7) were used at 750 nM and 188 nM, respectively. Bumper primers B1c 5'-dTAAACATGAAAACTCGTTCCG (SEQ ID NO: 8) and B2c 5'-dTTTTATGATGAGAACACTTAAACTCA (SEQ ID NO: 9) were used at 75 nM each. Final SDA conditions included 40 mM KPi (pH 7.5), 6.5 mM (Mg(OAc)2, 1.4 mM dCTPαS, 0.2 mM each dATP, dTTP and dGTP, 3% (v/v) DMSO, 8.2% (v/v) glycerol, 50 ng/uL human placental DNA, 0.5 U/uL BST, 4.5 U/uL Aval, 1% (w/v) trehalose, and 50 ug/mL BSA.

Devices and Instrumentation

The same devices and instrumentation as were used in Example 1 were used in this Example, except that aliquots (4 uL) of dry-down mix consisting of 20 mM KPi, 10 ng/mL human placental DNA, 2.5 U/uL BST, 22.5 U/uL Aval, 2 mM Mg(OAc)$_2$, 5% (w/v) trehalose, and 0.02 mg/mL BSA were dried at 37° C. under controlled low humidity to glassy films in the sample compartments of the DNA Cards.

Procedure

Rehydration mix consisting of chlamydia target, 36 mM KPi, 1.4 mM dCTPαS, 0.2 mM each dATP, dTTP and dGTP, 3% (v/v) DMSO, 8.2% (v/v) glycerol, 400 nM FAM-Rox detector probe (5'(FAM)dTAGCACCCGAGTGCT(ROX) AGAGTCTTCAAATATCAGAG CTTTACCTAACAA (SEQ ID NO: 10), primers (S1.1, S2.1) and bumpers (B1c, B2c) at the concentrations listed above, 48 ng/uL human placental DNA, 6.1 mM Mg(OAc)$_2$, and 46 ug/mL BSA was heat denatured at 97° C. for 2 minutes and added to prewarmed DNA Cards at 55° C. Sealer strips were applied and the fluorescence monitored at 485 (EX)/535 (EM) nm on the fluorometer instrument.

Results and Conclusions

Figure 4:
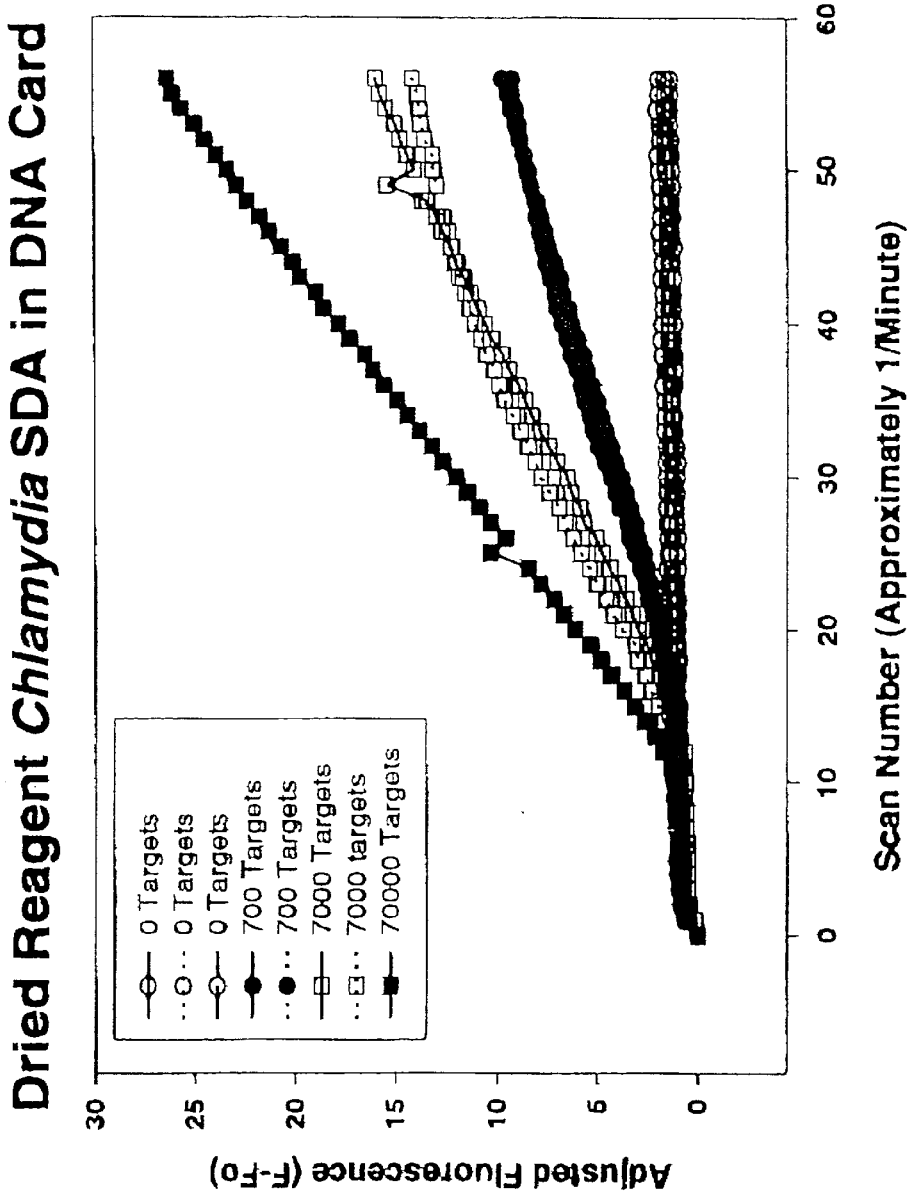
FIG. 4 depicts the results of an experiment in which an amplification and homogeneous fluorescence real time detection assay was conducted wherein a Chlamydia nucleic acid sequence was amplified with a rehydrated fluorescence probe.

As shown in FIG. 4, inspection of the resulting fluorescence signal showed only small fluctuations until evidence of amplification specific fluorescence change became evident. In each case, the amount of fluorescence change was proportional to the target added. Thus, any such fluctuation could be compensated by numerical algorithm.

EXAMPLE 5

Practical Kit Application of Method for Amplification and Homogeneous Fluorescence Real Time Detection of a *Neisseria gonorrhoeae* Target Analyte Nucleic Acid Sequence The results of Examples 3 and 4 above showed the utility of a method for amplification and homogeneous fluorescence real time detection of a target nucleic acid sequence in which rehydration of a fluorescence probe was conducted separate from, and prior to the amplification reaction. However, the method was not conducted in a format which would be considered optimal for a typical practitioner.

Thus, a kit was developed in which a first vessel contained certain reagents for such a reaction, such as, for example, the primers for the amplification as well as the fluorescence probe in a dry form, but a reagent or condition that would cause commencement of the amplification reaction was omitted. Therefore, the fluorescence probe was rehydrated by addition of sample, but amplification did not commence until exposure of the rehydrated probe mixture to such a reagent or condition.

Specifically, a kit including two corresponding microtiter plates was developed. The wells of the first microtiter plate contained the primers and the fluorescence probe, and the wells of the second microtiter plate contained the enzymes for the amplification reaction. More specifically, a kit and method for the amplification and homogeneous fluorescence real time detection of Neisseria gonorrhoeae nucleic acid was developed as follows.

Materials and Methods

The first microtiter plate contained, in each well, in a single dry spot, the following constituents:

37.5 mnM potassium phosphate, pH 7.6

3.5% trehalose 0.19 mg/ml acetylated BSA 0.675 mM DTT 3.75 mM magnesium acetate 1.9 uM first amplification primer GCIR-AL5.3 (5'CGATTCCGCTCCAGACTTCTCGGGAACAGC-TTGAAGTTTT3') (SEQ ID NO: 11)

1.9 uM second amplification primer GCIR-AR5.1 (5'ACCGCATCGAATGCATGTCTCGGGTCCTTG-CAGTTAGGC3') (SEQ ID NO: 12)

0.19 uM first bumper GCIR-BL5.1 (5'CGCAAATCATCAAAG3') (SEQ ID NO: 13)

0.19 uM second bumper GCIR-BR5.1 (5'TCAAGACGCTTCACG3') (SEQ ID NO: 14)

0.75 uM FamRox detector probe GCIR5-FD10 (5'TAGCACCCGAGTGCTTTCTCCGTCTGCTCTT-TTATCTTCTC3') (SEQ ID NO. 15)

0.94 mM dUTP 3600 ng crude dialyzed human placental DNA

The second microtiter plate contained, in each well corresponding to a first well, in a single dry spot, the following constituents:

25 mM potassium phosphate, pH 7.6

2.3% trehalose 0.125 mg/ml acetylated BSA 0.45 mM DTT 10 mM magnesium acetate 320 units BsoB1, 20 units Bst polymerase 1.75 mM dCsTP 0.25 mM dATP 0.25 mM dGTP The following protocol was then practiced:

Aliquots (~150 ul) of a sample containing a plasmid GC10 were dispensed into each well of the first microtiter plate. GC10 contains an 800 base pair region of the Neisseria gonorrhoeae genome inserted into PUC18.

The wells of the first microtiter plate were covered, and the plate was retained at room temperature for 20 minutes. The first microtiter plate was then uncovered, and incubated at 75° C. for 10 minutes, while the second microtiter plate was pre-warmed for 10 minutes to 52° C.

After the 10 minute incubation, 100 ul aliquots from each well of the first microtiter plate were transferred (pipetted) to a corresponding well in the second microtiter plate. The second microtiter plate was then sealed with an adhesive cover, and introduced into a fluorescence reader instrument as described in co-pending U.S. patent application Ser. No. 08/929,895, filed Sep. 15, 1997, the disclosure of which is specifically incorporated herein by reference. (Other standard microtiter plate fluorescence reader instruments could also be used.)

The fluorescence signal from the wells of the second microtiter plate were monitored for 60 minutes. The sealed second microtiter plate was then discarded in a sealed bag to further insure against potential amplicon contamination of the laboratory environment.

Results and Conclusions

The fluorescence signal from the wells showed steady increase over time, and the signal did not exhibit uncorrectable, variable signal fluctuation as was seen in Examples 1 and 2.

EXAMPLE 6

Practical Kit Application of Method for Amplification and Homogeneous Fluorescence Real Time Detection of a *Chlamydia trachomatis* Target Analyte Nucleic Acid Sequence As in Example 5, a kit including two corresponding microtiter plates was developed. The wells of the first microtiter plate contained the primers and the fluorescence probe, and the wells of the second microtiter plate contained the enzymes for the amplification reaction. More specifically, a kit and method for the amplification and homogeneous fluorescence real time detection of Chlamydia trachomatis cryptic plasmid nucleic acid was developed as follows.

Materials and Methods

The first microtiter plate contained, in each well, in a single dry spot, the following constituents:

37.5 mM potassium phosphate, pH 7.6
3.5% trehalose
0.19 mg/ml acetylated BSA
0.675 mM DTT
3.75 mM magnesium acetate
1.9 uM first amplification primer CtpF8.AL1 (5'CGATTCCGCTCCAGACTTCTCGGGACAAAA-TCAACACCTG3') (SEQ ID NO: 16)
1.9 uM second amplification primer CtpF8.AR1 (5'ACCGCATCGAATGCATGTCTCGGGGAGACT-GTTAAAGATA3') (SEQ ID NO: 17)
0.19 uM first bumper CtpF8.BL (5'CAGCAAATAATCCTTGG3') (SEQ ID NO: 18)
0.19 uM second bumper CtpF8.BR (5'CATTGGTTGATGAATTATT3') (SEQ ID NO: 19)
0.75 uM FamRox detector probe CtpF8.FD1 (5'TAGCACCCGAGTGCTCGCAGCCAAAATGAC-AGCTTCTGATGGAA3') (SEQ ID NO. 20)
0.94 mM dUTP
3600 ng crude dialyzed human placental DNA The second microtiter plate contained, in each well corresponding to a first well, in a single dry spot, the following constituents:

25 mM potassium phosphate, pH 7.6
2.3% trehalose
0.125 mg/ml acetylated BSA
0.45 mM DTT
10 mM magnesium acetate
320 units BsoB1, 20 units Bst polymerase
1.75 mM dCsTP
0.25 mM dATP
0.25 mM dGTP The following protocol was then practiced:

Aliquots (~150 ul) of a sample containing a plasmid pCT16 were dispensed into each well of the first microtiter plate. pCT16 contains regions B and F of the Chlamydia trachomatis cryptic plasmid (from Serovar J) inserted into pUC18.

The wells of the first microtiter plate were covered, and the plate was retained at room temperature for 20 minutes. The first microtiter plate was then uncovered, and incubated at 75° C. for 10 minutes, while the second microtiter plate was pre-warmed for 10 minutes to 52° C.

After the 10 minute incubation, 100 ul aliquots from each well of the first microtiter plate were transferred (pipetted) to a corresponding well in the second microtiter plate. The second microtiter plate was then sealed with an adhesive cover, and introduced into a fluorescence reader instrument as described in co-pending U.S. patent application Ser. No. 08/929,895, filed Sep. 15, 1997, the disclosure of which is specifically incorporated herein by reference. (Other standard microtiter plate fluorescence reader instruments could also be used.)

The fluorescence signal from the wells of the second microtiter plate were monitored for 60 minutes. The sealed second microtiter plate was then discarded in a sealed bag to further insure against potential amplicon contamination of the laboratory environment.

Results and Conclusions

As in Example 5, the fluorescence signal from the wells showed steady increase over time, and the signal did not exhibit uncorrectable, variable signal fluctuation as was seen in Examples 1 and 2.

While the invention has been described with some specificity, modifications apparent to those with ordinary skill in the art may be made without departing from the scope of the invention. Various features of the invention are set forth in the following claims.

What is claimed is:

1. A method for conducting a fluorescence detection assay to determine the presence, absence, or amount of a target analyte in a sample, said method comprising:
   (a) producing a mixture by exposing the sample to a first reagent formulation comprising a dry, hydratable binding partner of said target analyte, said binding partner (i) being capable of producing a detectable change of fluorescence signal as the amount of target analyte changes, and (ii) being hydrated by exposure to said sample; and
   (b) exposing said mixture to a second reagent formulation or a condition, which, if said target analyte is present in the sample, then the amount of said target analyte will change.

2. The method of claim 1, wherein said target analyte is a nucleic acid molecule.

3. The method of claim 2, wherein said binding partner is a nucleic acid molecule comprising a sequence which hybridizes to the sequence of the target analyte.

4. The method of claim 3 wherein said binding partner comprises a fluorescence energy donor moiety and a fluorescence energy acceptor moiety in sufficiently close proximity that a decrease of such proximity results in the detectable change of fluorescence signal.

5. The method of claim 2, wherein said first reagent formulation further comprises primers for a nucleic acid amplification reaction.

6. The method of claim 5, wherein said binding partner and said primers are in a dry form.

7. The method of claim 2, wherein said second reagent formulation comprises an enzyme necessary for a nucleic acid amplification reaction.

8. The method of claim 7 wherein said enzyme is a polymerase.

9. The method of claim 8 wherein said polymerase is in a dry form.

10. The method of claim 1 wherein said condition is a change of temperature.

11. The method of claim 10 wherein said change of temperature is an increase of temperature.

12. The method of claim 1, further comprising:
   (c) containment of said mixture after exposure to said second reagent formulation or said condition.

* * * * *